(12) United States Patent
Wang et al.

(10) Patent No.: US 10,147,187 B2
(45) Date of Patent: Dec. 4, 2018

(54) KIND OF DR RADIOGRAPHY LUNG CONTOUR EXTRACTION METHOD BASED ON FULLY CONVOLUTIONAL NETWORK

(71) Applicant: SICHUAN UNIVERSITY, Chengdu, Sichuan (CN)

(72) Inventors: Junfeng Wang, Chengdu (CN); Peng Tang, Chengdu (CN); Fan Li, Chengdu (CN); Yihua Du, Chengdu (CN); Yulin Ji, Chengdu (CN); Zongan Liang, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 15/598,628

(22) Filed: May 18, 2017

(65) Prior Publication Data

US 2018/0130202 A1    May 10, 2018

(30) Foreign Application Priority Data

Nov. 4, 2016  (CN) .......................... 2016 1 0973463

(51) Int. Cl.
| | |
|---|---|
| *G06K 9/00* | (2006.01) |
| *G06T 7/00* | (2017.01) |
| *G06T 7/13* | (2017.01) |
| *A61B 6/00* | (2006.01) |

(52) U.S. Cl.
CPC .............. *G06T 7/0012* (2013.01); *A61B 6/50* (2013.01); *A61B 6/5211* (2013.01); *G06T 7/13* (2017.01); *G06T 2207/10116* (2013.01); *G06T 2207/20081* (2013.01); *G06T 2207/20084* (2013.01); *G06T 2207/30061* (2013.01)

(58) Field of Classification Search
CPC . G06T 2207/10116; G06T 2207/20081; G06T 2207/20084; G06T 2207/30061; G06T 7/0012; G06T 7/13; A61B 6/50; A61B 6/5211
See application file for complete search history.

(56) References Cited

U.S. PATENT DOCUMENTS

| | | | |
|---|---|---|---|
| 8,989,469 B2 * | 3/2015 | Fahimian | A61B 6/032 378/19 |
| 2017/0249744 A1 * | 8/2017 | Wang | G06T 7/11 |

* cited by examiner

*Primary Examiner* — Amara Abdi
(74) *Attorney, Agent, or Firm* — Oliff PLC

(57) ABSTRACT

A DR radiography lung contour extraction method based on fully convolutional network, which includes the steps: Establish the fully convolutional network structure of lung contour segmentation; Conduct off-line training on the weighting parameters of the fully convolutional network; Read DR image and weighting parameters of the fully convolutional network; Input DR image into fully convolutional network and output segmentation results of image through network terminal with network layer-by-layer feedforward. Establish lung contour in accordance with segmentation results.

9 Claims, 3 Drawing Sheets

Figure 1:
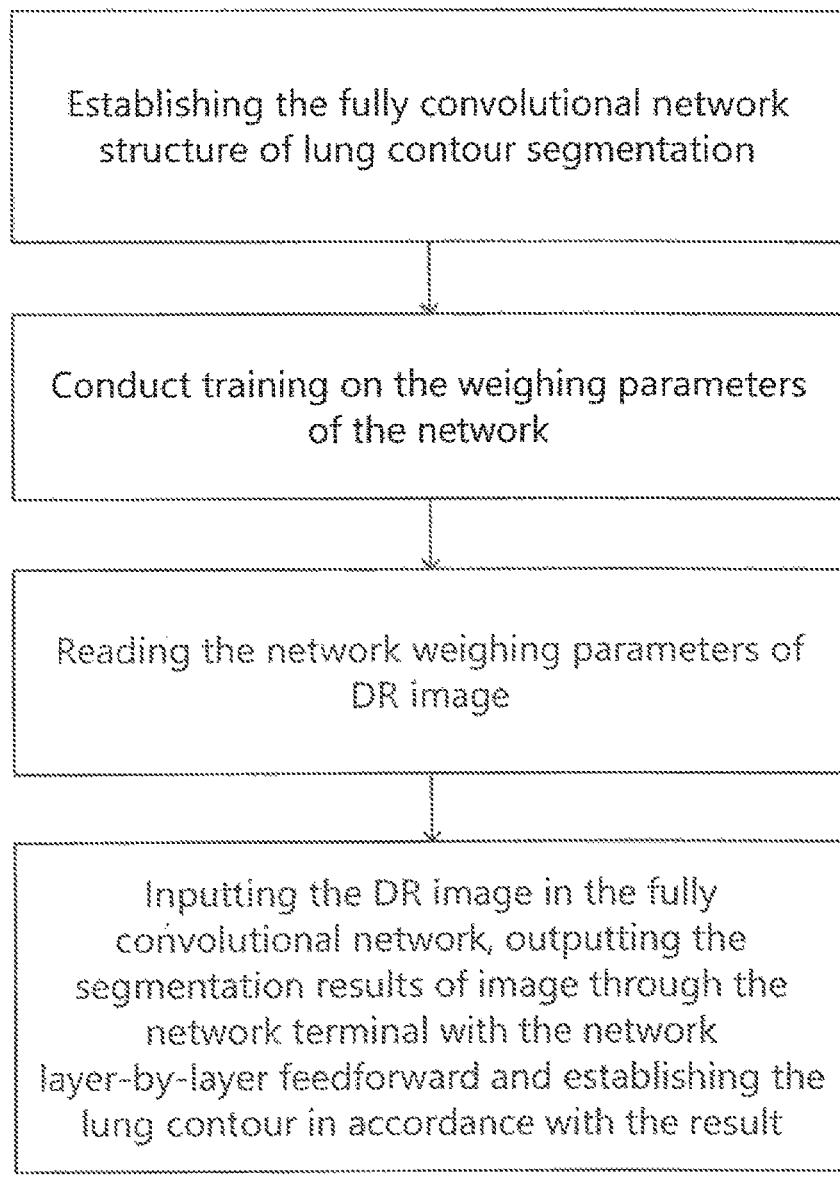

KIND OF DR RADIOGRAPHY LUNG CONTOUR EXTRACTION METHOD BASED ON FULLY CONVOLUTIONAL NETWORK

FIELD OF TECHNOLOGY

This invention involves the image treatment field especially involves a kind of DR radiography lung contour extraction method based on fully convolutional network.

BACKGROUND TECHNOLOGY

The radiography image of chest is the key technology of diagnosis for the pulmonary disease. X-ray imaging is the main measures to the medical screening of pulmonary diseases such as the pulmonary inflammation, lump, tuberculosis, lung cancer and so on; Along with the development of digital imaging technology, the digital radiography i.e. DR (Digital Radiography) gradually replaces the traditional chest perspective imaging method; DR refers to a new technology of directly conducting digital X-ray photography under the control of computers, which means to convert the X-ray information which penetrates the human body into the digital signal by adopting amorphous silicon flat-panel detectors, rebuild the image through the computer and conduct a series of image post-processing; The DR system is mainly composed of several parts such as the X-ray generation device, direct conversion flat panel detector, system controller, image monitor, image treatment working station and so on; As the DR technical dynamic range is wide and the X-ray light quantum detection efficiency (DQE) is high, it has quite a large latitude in exposure. Even though the condition of exposure is slightly bad, the excellent images can be obtained; DR imaging has high sharpness and low radiation, which has become the mainstream technical device in a lot of hospitals and the grassroots physical examination centers in our country.

In our country, the general purpose of shooting chest DR image is to conduct the screening of the serious and infectious diseases such as tuberculosis or lung cancer and etc; The tuberculosis is caused by the mycobacterium tuberculosis, which is easily spread through spray in the air and even the aerosol; The majority of tuberculosis patients is young adults, which will result in the labor loss for the families and the society; The world health organization indicates that the tuberculosis is the important public health problem all over the world. In our country, there are approximately 5000000 active pulmonary tuberculosis patients at present and there are $5*10^4$ people die of tuberculosis every year; The tuberculosis is one of the main infectious disease which is importantly prevented and controlled in our country; In consideration of the fact that the damage of the tuberculosis is serious and the difficulty of the prevention and control work is big while the scale of local tuberculosis prevention and control teams at different levels is still small, whose power and expenditure cannot adapt the prevention and control demand, the technology and capital input shall be strengthened and the medical prevention combination mechanism shall be established to form the practical and effective prevention and treatment system; At present, two weak and difficult links of early-stage notice and treatment management exist in the implementation of the prevention and treatment for the tuberculosis; Under such circumstance, the screening program for the tuberculosis patients among the focus groups is gradually launched inside the country by using the essential public health service; Being compared with the tuberculosis, the severity degree of damage to the lung cancer on the health of the patients is higher than that of the former; It is universally acknowledged that the death rate of lung cancer is considerably higher than that of other cancers and it increases by years in recent years; The imageological examination is one of the important technical measures in the aspects of diagnosis, test, prevention and treatment on the cancer; The generally major research object of chest imaging is the lung cancer, which normally observes the corresponding lung images through establishing the lung window; Lung cancer is a neoplastic disease which is related to the smoking, atmospheric pollution and low immunologic function; For example, the repeated inflammatory stimulation of factors like the dust-haze in recent years will bring the chronic damage, affecting the normal epithelial function of the bronchial epithelium and the immune antiviral state of the body and having facilitation affect on the occurrence of lung cancer.

The principle of DR radiography imaging is that the human tissue has difference of density and thickness. When the X-ray penetrates different tissues of the human body, the absorption degrees of X-ray vary. Thus, the quantity of X-ray that reaches the screen varies and form the images with different grayscale intensity; It uses the imaging differences of different density to the human tissue under the X-ray to analyze the thickness and density difference of the tissues, speculates and evaluates the possible diseased region therein to offer basis for the diagnosis for the doctors; However, the structure of human tissue is complicated. The thoracic cavity and enterocoelia include the key organs of the human body, which include all kinds of visceral organs with high density and low density; Therefore, the images of all organs and tissues overlap with each other, which has quite a large influence on the observation and judgment; So the reading and judgment of the DR radiography have very high requirement on the experience and vigor of the doctors, in which the early stage and atypical cases are easy to be ignored. Although the DR radiography examinations of certain size are conducted in the primary hospitals and medical examination points, the DR radiography examinations of extra large scale are very hard to be truly launched with the current existing labor and technical resources.

Although the reading and diagnosis of DR radiography has large difficulty, the digital technology adopted by it offers the basic technical conditions for the post-treatment to the targeted images in accordance with the clinical demand; The image post-treatment is the largest characteristic of digital images; The targeted treatment can be conducted on the images in accordance with the diagnosis demand through developing algorithm and software function only if the original data is reserved, which improves the diagnostic rate; Under the current technical conditions, the targeted DR radiography image treatment and analysis still have difficulty; The existing devices can only realize the functions in generic form of the DR radiography such as enhancing the sharpness of edges, magnifying the roaming, image stitching, adjustment of window width and window level in region of interest, etc. or the measurement of the basic distance, area and density; The difficult realization of the atopic functions aiming at the specific organs or lesions type is resulted from the fact that the image treatment technology aiming at the tasks and objects still have a lot of technical difficulty in the application layer; As far as the chest DR radiography, one major difficulty point of the intelligent interpretation to the digital images is how to determine the area of lung lobe; If the scope of lung lobe can be accurately confirmed and the interference outside the lung can be weakened or eliminated, it will be more beneficial for the notice of slight lesion; In addition, the shape of the lung lobe contour itself also is the important factor of judging relevant physiological index of the people receiving physical examination; Reliable lung lobe contour extraction algorithm can reduce the time of rechecking for the people receiving physical examination and reduce the number of chest images, letting theirs obtain the definite diagnosis on their nidus from the doctors at the cost of lower radiation dosage; At present, there is no lung lobe contour extraction method that aims to the treatment of DR radiography.

CONTENTS OF THE INVENTION

This invention offers a kind of DR radiography lung contour extraction method based on fully convolutional network which improves the screening treatment efficiency of pulmonary disease and improves the detection accuracy of nidus and the monitoring efficiency of serious infectious disease.

The technical program adopted in this invention is a kind of DR radiography lung contour extraction method based on fully convolutional network, which comprises the steps as follows:

Establish the fully convolutional network structure of lung contour segmentation;

Conduct off-line training on the weighting parameters of the fully convolutional network;

Read the DR image and the weighting parameters of the fully convolutional network;

Input the DR image into the fully convolutional network, output the segmentation results of image through the network terminal with the network layer-by-layer feedforward and establish the lung contour in accordance with the segmentation results.

Further, the mentioned fully convolutional network takes the layer of network as the unit. In accordance with the order form input to output, it includes the data layer, CONV1-MAXPOOL1-RELU1 layer, CONV2-MAXPOOL2-RELU layer, CONV3-MAXPOOL3-RELU3 layer, CONV4-MAXPOOL4-RELU4 layer, FC1 layer, Dropout1 layer, FC2 layer, Dropout2 layer, DECONV1 layer, Crop1 layer, FUSE1 layer, DECONV2 layer, Crop2 layer, ADD1 layer, DECONV3 layer, Crop3 layer and SoliMax layer.

Further, the mentioned offline training on the weighting parameters of the fully convolutional network comprises the steps as follows:

A. Collect certain DR image as the sample dataset;
B. Conduct the marking of lung lobe contour for the data in the sample dataset;
C. Extract the contour in the contour marketing, distinguish the left and right lung contours in accordance with the barycenter and form the left and right contour groups;
D. Randomly divide the left and right contour groups into the test sets of training sets;
E. Input the left and right lung contours in the fully convolutional network, calculate the output value, compare it with the marketing result and calculate the overall difference value;
F. Conduct inverse information propagation on the fully convolutional network and calculate the parameter updating of all network layers;
G. Return to Step E if the iterations do not reach the set value, otherwise enter into Step H;
H. Obtain the network loading parameter value is are needed.

Further, the following treatment shall be conducted on the image for one time before inputting the mentioned DR image in the fully convolutional network:

Convert the DR image into the floating-point type matrix;
Conduct the dimension standardization treatment on the floating-point matrix;
Conduct the whitening treatment of the DR image.

Further, the soft maximum value algorithm Softmax is adopted in the calculation method of the mentioned overall difference value.

Further, the batch random gradient descent algorithm Batch-SGD is adopted in the mentioned calculation for the parameter updating of all network layers.

Further, the conversion method of the mentioned floating-point type matrix is: Dividing the 12-bits or 14-bits depth pixel value of image in DICOM format by $2^{12}$ or $2^{14}$ and converting it to the floating-point type matrix.

Further, the method of the mentioned dimension standardization treatment is to resize the image to the pixel dimension of 512×512 by adopting the Gaussian smoothing algorithm Gaussian.

Further, the method of the mentioned whitening treatment is to deduct the mean value of all training samples from the image digitized by the floating point of the standardization dimension and then divide it by the standard deviation of all training samples.

The beneficial effects of this invention are as follows:

(1) This invention makes the subsequent lung disease more targeted through extracting the lung contour, which improves the reliability and accuracy of the computer auxiliary treatment; It can reduce the visual working load of the doctors and improve the overall recognition accuracy and treatment efficiency; And it reduces the influence of the experience difference of the doctors on the judgment for the state of an illness;

(2) This invention can automatically treat the chest DR radiography, adapt the DR radiography of different devices and adapt different figures, genders and ages of the photographer;

(3) This invention can effectively utilize the network resources, realize the remote consultation and return visit for the disease, improving the reliability to the consultation of the difficult and complicated disease;

(4) This invention can serve as the basis of the computer auxiliary diagnosis, whose images without interference of ribs will be helpful for the design of the subsequent automated lesion judgment method;

(5) This invention integrates the current medical device and information network resources, improving the usage rate of the device and preventing the idle device and the resource waste.

SPECIFICATION OF THE ATTACHED FIGURES

Figure 2:
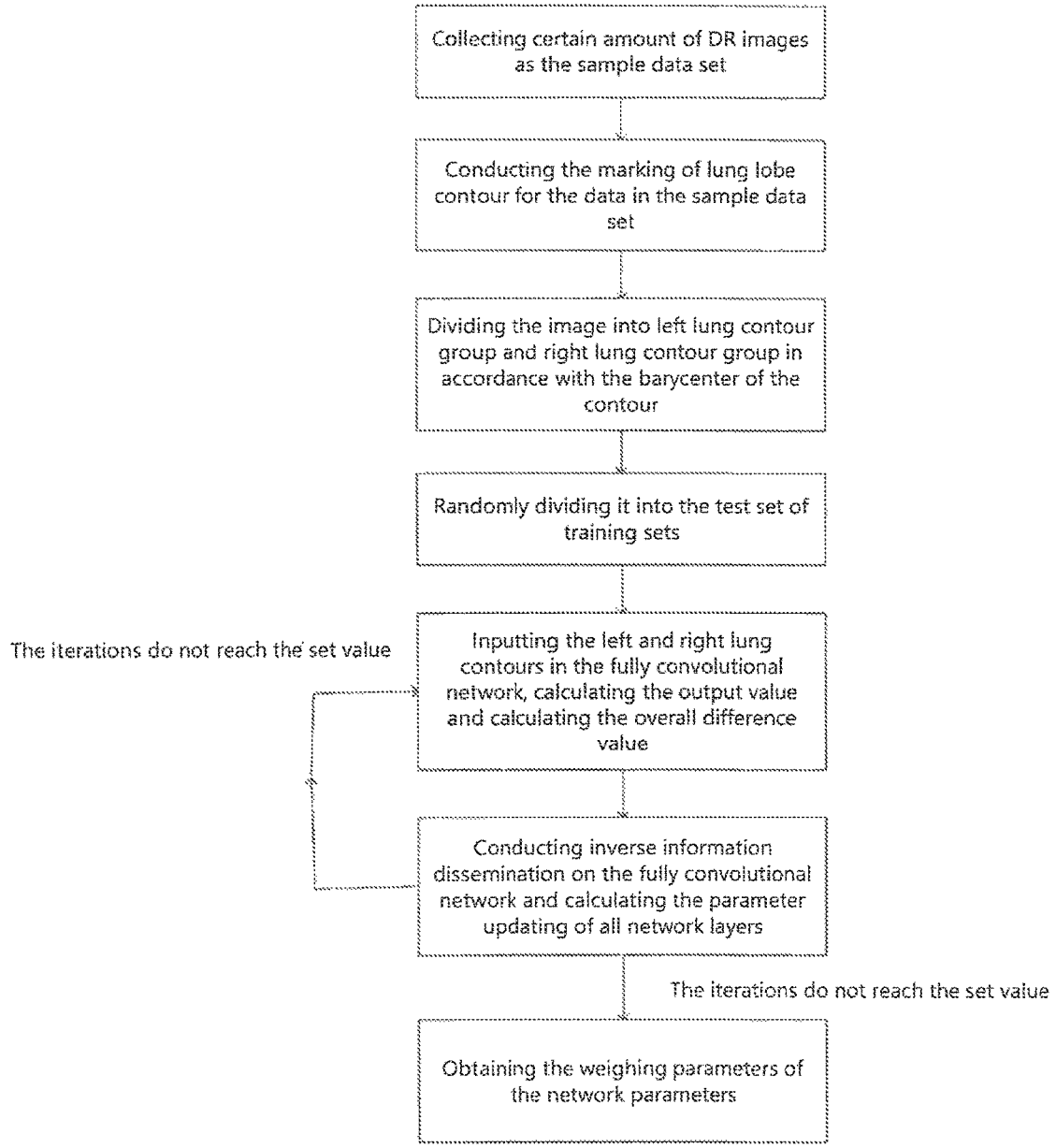
Figure 3:
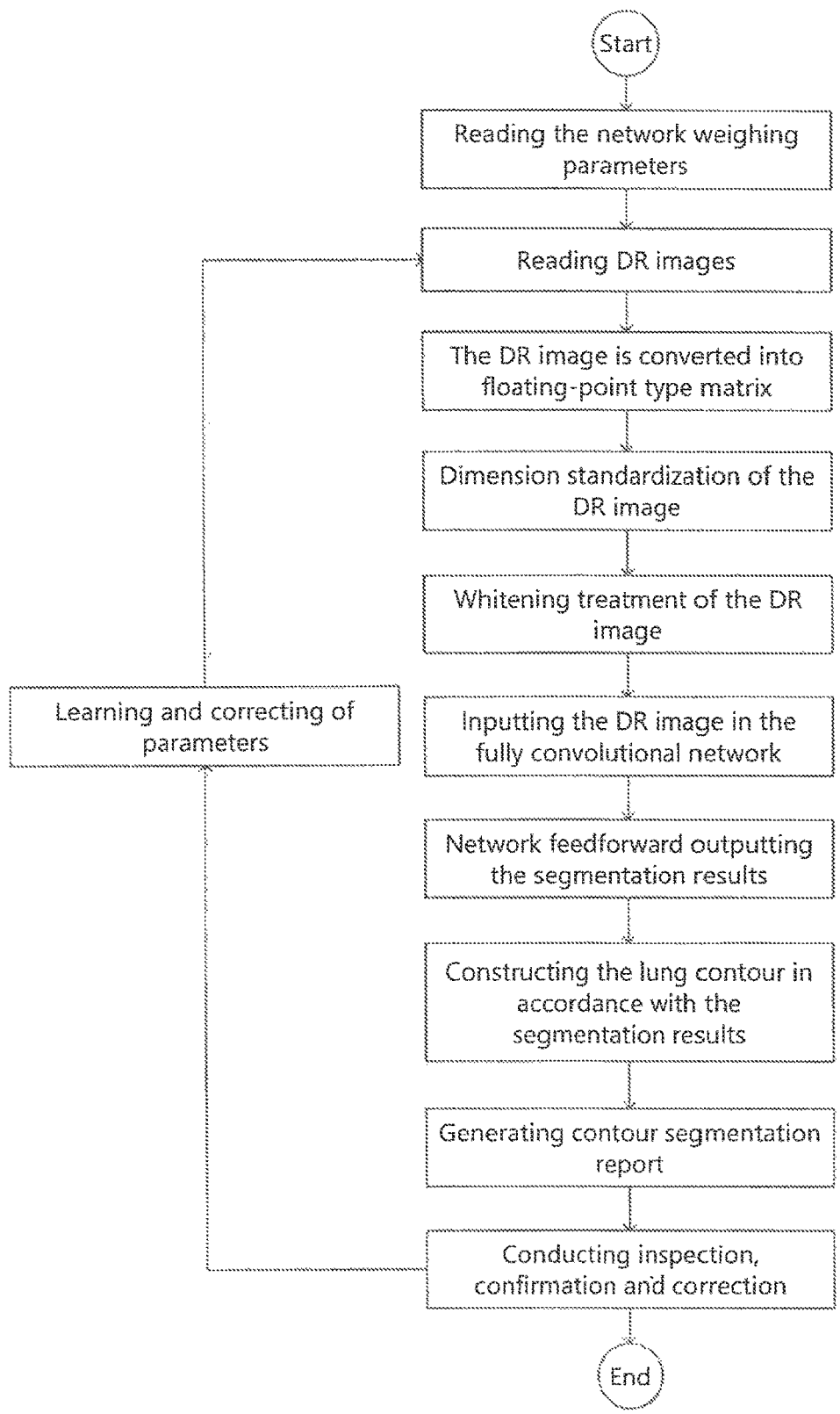

FIG. 1 shows the flow diagram of this invention.
FIG. 2 shows the offline training flow diagram of the weighting parameters in the fully convolutional network.
FIG. 3 shows the treatment flow of the lung contour automatic extraction method of the chest DR radiography.

SPECIFIC IMPLEMENTATION METHOD

This invention adopts the computer image treatment technology to obtain the possible lung contour boundary and the subsequent area of DICOM (Digital Imaging and Communications in Medicine i.e. medical digital imaging and communications) images and conducts further filtering to get the optimum matching scheme in the candidate region with high possibility, solving the problem that the data size of the current large-scale residents medical examination is so large that the doctors are very hard to keep the detection with high accuracy due to the manual mark one by one in the limited time; it utilizes the advantage of medical informatization, which can adapt the problems such as the difference resulted from the subjective factors of the medical personnel, device change of the medical examination points, the computer level difference of the operation staff and so on; The whole treating process is easy and convenient, which can fundamentally improve the treating efficiency of the tuberculosis screening while reducing the workload of the medical workers in the medical examination points. Thus, the computer auxiliary screening can be promoted to the grass-root medical organizations which are lack of evaluation experience for the tuberculosis chest X-ray imaging in time, which is more beneficial to the further normalization and standardization of the targeted resident scale medical examination on the important infectious disease.

This invention can automatically treat all kinds of chest X-ray DR image and extract the lung lobe contour; This invention can reduce the workload for manual detection on the chest X-ray imaging of the medical workers through using new technical measures and improves the detection accuracy of nidus and the monitoring efficiency of serious infectious disease, offering information basis for the for the developing of program decisions to the prevention and control of infectious disease and for the adjustment for the policies of the public hygiene and health.

It is a kind of DR radiography lung contour extraction method based on fully convolutional network, which comprises the steps as follows:

Establish the fully convolutional network structure of lung contour segmentation;

Conduct off-line training on the weighting parameters of the fully convolutional network;

Read the DR image and the weighting parameters of the fully convolutional network;

Input the DR image into the fully convolutional network, output the segmentation results of image through the network terminal with the network layer-by-layer feedforward and establish the lung contour in accordance with the segmentation results.

Further, the mentioned fully convolutional network takes the layer of network as the unit. In accordance with the order form input to output, it includes the data layer, CONV1-MAXPOOL1-RELU1 layer, CONV2-MAXPOOL2-RELU layer, CONV3-MAXPOOL3-RELU3 layer, CONV4-MAXPOOL4-RELU4 layer, FC1 layer, Dropout1 layer, FC2 layer, Dropout2 layer, DECONV1 layer, Crop1 layer, FUSE1 layer, DECONV2 layer, Crop2 layer, ADD1 layer, DECONV3 layer, Crop3 layer and SoftMax layer.

This invention first establishes the fully convolutional network RN-LUNG structure of lung contour segmentation; This network structure is the basis of realizing this invention, which keeps stable and unchanged during the process of use and takes the layer of network as unit. In accordance with the order form input to output, it includes the following structure:

1. The data layer is input the gray scale image matrix of 512×512 pixel in the single channel with the matrix data type as the floating-point type.

2. The CONV1-MAXPOOL1-RELU1 layer is constituted of the convolutional layer, pooling layer and the ReLU activation layer. Therein, the convolution operator dimension of the convolutional layer is 20×9×9 and every pixel of 2×2 in the pooling layer is aggregated to 1 pixel and the maximum value therein is taken.

3. The CONV2-MAXPOOL2-RELU2 layer is constituted of the convolutional layer, pooling layer and the ReLU activation layer. Therein, the convolution operator dimension of the convolutional layer is 40×7×7 and every pixel of 2×2 in the pooling layer is aggregated to 1 pixel and the maximum value therein is taken.

4. The CONV3-MAXPOOL3-RELU3 layer is constituted of the convolutional layer, pooling layer and the ReLU activation layer. Therein, the convolution operator dimension of the convolutional layer is 80×5×5 and every pixel of 2×2 in the pooling layer is aggregated to 1 pixel and the maximum value therein is taken.

5. The CONV4-MAXPOOL4-RELU4 layer is constituted of the convolutional layer, pooling layer and the ReLU activation layer. Therein, the convolution operator dimension of the convolutional layer is 160×5×5 and every pixel of 2×2 in the pooling layer is aggregated to 1 pixel and the maximum value therein is taken.

6. The FC1 layer is the fully connection layer which realizes the convolution with convolution kernel size of 1×1 and is output as 1024 layers.

7. The Dropout1 layer realizes the zero setting of partial parameters of 50% concepts.

8. The FC2 layer is the fully connection layer which realizes the convolution with convolution kernel size of 1×1 and is output as 2048 layers.

9. The Dropout2 layer realizes the zero setting of partial parameters of 50% concepts.

10. The DECONV1 layer calculates the inverse convolution output image through the inverse convolution operator of dimension as 10×10 and the interval of step length as 8 with 50 output layers.

11. The Crop1 layer cuts out the output results of DECONV1 layer, making the pixel dimension of length and width to its output image consistent with that of the CONV3-MAXPOOL3-RELU3 layer.

12. The FUSE1 layer pluses the value of the output result of Crop1 layer by the output value of CONV3-MAXPOOL3-RELU3 layer in the corresponding pixel position.

13. The DECONV2 layer calculates the inverse convolution output image through the inverse convolution operator of dimension as 10×10 and the interval of step length as 8 with 20 output layers.

14. The Crop2 layer cuts out the output results of DECONV2 layer, making the pixel dimension of length and width to its output image consistent with that of the CONV1-MAXPOOL1-RELU1 layer.

15. The ADD1 layer pluses the value of the output result of Crop2 layer by the output value of CONV1-MAXPOOL1-RELU1 layer in the corresponding pixel position.

16. The DECONV3 layer calculates the inverse convolution output image with the result of ADD1 layer as the output through the inverse convolution operator of dimension as 5×5 and the interval of step length as 4 with 3 output layers, which correspond with the left lung, right lung and the background area respectively.

17. The Crop3 layer cuts out the output results of DECONV3 layer, making the pixel dimension of length and width to its output image consistent with the output of the data layer.

18. The SoftMax layer calculates the soft maximum value Softmax of Crop3 layer, which is used to assess the accuracy of the output result.

After the topology stricture of the segmentation network of lung contour is established, the lung contour DR image data set with marks shall be utilized offline to train the weighting parameters of the segmentation network of lung contour, gaining the feature expression of the contour; Therein, the lung DR image data set with marks includes two parts, which are the DR radiography and the corresponding contour marking images; The offline training process of the network weighting parameters includes the steps as follows:

A. Collect certain DR image as the sample data set; Under normal situation, the quantity of the DR images in the data set shall be more than 5000;

B. Conduct the lung lobe contour marking for the images in the sample data set; Through marking software, manually draw the black and white image corresponding with the sample, in which the white area corresponds with the lung lobe area and the black area corresponds with other areas; Save the file of black and white image as the contour marks of the sample lung lobe in the data set;

C. Extract the contour in the contour marks and form the left and right lung contour sets in accordance with its barycenter area; Conduct traversal on all marked images in the data set, extract the contour in every contour marking image, distinguish the left and right lung contours in accordance with the barycenter of the contour and respectively add the pixel groups of the left and right lung contours to the left lung contour group and right lung contour group according to the left and right;

D. Randomly divide the left and right lung contour groups into the test sets of training set; Therein, the test sets occupy about 20% of the total data amount;

E. Input the left and right lung contours in the test sets of training sets in the fully convolutional network, calculate the overall difference value after comparing its output value with the marked results; After inputting them to the fully convolutional network, calculate its output and compare the output value with the manual marking results. Then use the soft maximum value algorithm Softmax to calculate the overall difference value;

F. Conduct inverse information spreading on the fully convolutional network and calculate the parameter updating of all network layers; Taking reducing the overall difference value in the last step as the target and adopt the batch random gradient descent algorithm Bach-SGD to calculate the parameter updating of all network layers;

G. If the iterations do not reach the set value, return to Step E and continue reading new samples for training, otherwise enter into Step H;

H. Obtain the network loading parameter value which is needed.

After the lung segmentation network topology structure and its weighting parameters are established, the system has the complete lung lobe contour segmentation ability; Herein, it can realize the online lung lobe image contour detection, i.e. transfer any newly input DR image into the network input and conduct feedforward layer by layer through the network, finally output the contour template image through the network terminal; The non-zero pixel gray scale connection areas therein respectively refer to the left and right lung lobe contours;

Further, the following treatment shall be conducted on the image for one time before inputting the mentioned DR image in the fully convolutional network:

Convert the DR image into the floating-point type matrix;

Conduct the dimension standardization treatment on the floating-point type matrix;

Conduct the whitening treatment of the DR image.

The treating steps for the contour online detection of the lung lobe image on this basis are as follows:

Initialization of extraction system to the lung lobe area in the chest DR radiography;

Read a DICOM image from the DR radiography database;

Divide the 12-bits or 14-bits depth pixel value of the DICOM image into $2^{12}$ or $2^{14}$ and converting it to the floating-point type matrix;

Resize the float point DICOM image to the pixel dimension of 512×512 by adopting the Gaussian smoothing algorithm Gaussian;

Conduct the whitening treatment on the float point DICOM image of standardization dimension, which means to deduct the mean value of all training samples from it and then divide it by the standard deviation of all training samples;

Input the data of test samples after whitening treatment in the FCN-LUNG network and calculate the output through the network feedforward;

Output the optimum matching value in accordance with the network, combine and generate the contour shape.

The method offered in this invention serves as the basic steps of the lung disease diagnosis. Combine this invention with the automated treatment of computer and corresponding programs, apply it in the large-scale screening of serious disease and infectious disease in the grassroots medical examination points, in which the devices conduct the detection steps as follows:

1) The workers in the medical examination points connect the computer which is equipped with DR radiography management module to the DR radiography database and configurate the parameters for the reading of DICOM image files;

2) Connect the computers in the medical examination points to the remote medical image data server;

3) After the medical examination is finished, the computers in the medical examination points automatically upload the newly added DR radiography on the same day to the remote server;

4) The system server receives the newly added DR radiography, labels them and add its labels in the pending queue, whose priority of treatment will be determined in accordance with the sequence of time;

5) When the system server scans the data which exists in the pending queue, it will automatically operate the automated extraction module of lung lobe contour and save the extraction results in the files;

6) After the system server conduct batch treatment on a certain quantity of DR images, it rill generate the fusion image typed treatment reports of DR original images and the contour extraction results;

7) In accordance with the medical records of the system grade, the system server sends the reports to different doctors, who will confirm the reliability of the segmentation results manually;

8) The doctors use the intelligent terminal to open the reports and they can click the confirmation button for the approved lung lobe contour extraction interface; For the unapproved segmentation results, they can choose the manual treatment or delay treatment in accordance with the difficulty degree of the DR images; Therein, the manual treatment normally aims at the intractable cases, for which the program interface of manual marks shall be opened manually to mark the lung lobe area; And the delay treatments is to re-insert the images in the pending queue but reduce its priority of treatment, making the system delay its treatment;

9) At the same time, the system supports the method of crossed evaluation, by which the lung contour with lower reliability of segmentation will be judged by multiple doctors;

10) The system will automatically call the self-adaptive updating module in accordance with the feedback from the doctors to improve the parameters of the current treating modules and conducts the deep process training based on the features of the images newly marked manually by the doctors during the period in which it does not serve for the user terminal devices of the doctors;

11) After the status updating of the system service, it will conduct retreatment on the residual images in the pending lists; Because of the optimizing to the system parameters, the lung field shape in the DR images which can not be treated originally can be extracted correctly in the improved system;

12) After the treatment of a certain batch to the DR radiography in the medical examination points ends, the system server will sends out the message about the ending of the treatment to the computers in the medical examination points and the information staff in the medical examination points will receive and process the results.

In every above step, the system will instruct the doctors for the remote operation in the way of graphical human-computer interaction and then they will automatically recognize and learn dynamically through the computers, which reduces the working frequency of manual intervention needed by the doctors, reduces the workload of the doctors and improves the treatment efficiency while improving the user experience, making the tedious marking and verification work easy to be accepted by people; In addition, the system adopts the browser—server (BS) framework, which allows the doctors to conduct marking and evaluation on the tuberculosis images on any computer which is connected to the Internet with user name and password only, making the working platform expand to the wide area universal network from the local private network; It not only is beneficial to the work and coordination of the doctors but also is helpful for the handling of the grass-roots work and the analysis and mining of the data for the local health authorities and disease control and prevention units.

This invention is a kind of algorithm and realization method that aims at the chest DR radiography digital images and utilizes the visual technology of the computer to extract the lung contour, which takes the medical image file in DICOM digital format as the object of treatment and takes the current existing medical image device, the computer servers and the Internet as the basis; Being combined with the current medical device and network resources, it can reduce the usage rate of the device, prevents the idle devices and resource waste and realizes the remote consultation and return visit of the diseases, improving the reliability of the consultation to the difficult and complicated diseases; This invention can serve as the basis of computer auxiliary diagnosis, which is helpful for the design of subsequent automated lesion judgment method; Also, being combined with the computer program, it can dynamically and continuously improve the system parameters in accordance with the feedback information of the doctors to improve the recognition performance.

The invention claimed is:

1. A digital radiology (DR) lung contour extraction method based on fully convolutional network, comprising the steps as follows:
   establish the fully convolutional network structure of lung contour segmentation;
   conduct off-line training on weighting parameters of the fully convolutional network;
   read a DR image and the weighting parameters of the fully convolutional network;
   input the DR image into the fully convolutional network, output segmentation results of image through a network terminal with a network layer-by-layer feedforward and establish the lung contour in accordance with the segmentation results.

2. The digital radiology (DR) lung contour extraction method based on fully convolutional network in claim 1, wherein the mentioned fully convolutional network takes the layer of network as the unit; wherein an order form input to output, it includes a data layer, CONV1-MAXPOOL1-RELU1 layer, CONV2-MAXPOOL2-RELU layer, CONV3-MAXPOOL3-RELU3 layer, CONV4-MAXPOOL4-RELU4 layer, FC1 layer, Dropout1 layer, FC2 layer, Dropout2 layer, DECONV1 layer, Crop1 layer, FUSE1 layer, DECONV2 layer, Crop2 layer, ADD1 layer, DECONV3 layer, Crop3 layer and SoftMax layer.

3. The digital radiology (DR) lung contour extraction method based on fully convolutional network in claim 1, wherein the mentioned offline training on the weighting parameters of the fully convolutional network comprises the steps as follows:
   A. Collect certain DR image as a sample data set;
   B. Conduct a marking of lung lobe contour for the data in the sample data set;
   C. Extract the contour in the contour marketing, distinguish a left and right lung contours in accordance with a barycenter and form a left and right contour groups;
   D. Randomly divide the left and right contour groups into a test sets of training sets;
   E. Input the left and right lung contours in the fully convolutional network, calculate an output value, compare it with a marketing result and calculate an overall difference value;
   F. Conduct inverse information dissemination on the fully convolutional network and calculate the parameter updating of all network layers;
   G. Return to Step E if the iterations do not reach the set value, otherwise enter into Step H;
   H. Obtain the network loading parameter value is are needed.

4. The digital radiology (DR) lung contour extraction method based on fully convolutional network in claim 1, wherein a following treatment shall be conducted on the image for one time before inputting the mentioned DR image in the fully convolutional network:
   Convert the DR image into a floating-point type matrix;
   Conduct a dimension standardization treatment on the floating-point type matrix;
   Conduct a whitening treatment of the DR image.

5. The digital radiology (DR) lung contour extraction method based on fully convolutional network in claim 3, wherein a soft maximum value algorithm Softmax is adopted in a calculation method of the mentioned overall difference value.

6. The digital radiology (DR) lung contour extraction method based on fully convolutional network in claim 3, wherein a batch random gradient descent algorithm Batch-SGD is adopted in the mentioned calculation for the parameter updating of all network layers.

7. The digital radiology (DR) lung contour extraction method based on fully convolutional network in claim 4, wherein the conversion method of the mentioned floating-point type matrix is: Dividing the 12-bits or 14-bits depth pixel value of image in DICOM format by 212 or 214 and converting it to the floating-point type matrix.

8. The digital radiology (DR) lung contour extraction method based on fully convolutional network in claim 4, wherein the method of the mentioned dimension standardization treatment is to resize the image to a pixel dimension of 512×512 by adopting the Gaussian smoothing algorithm Gaussian.

9. The digital radiology (DR) lung contour extraction method based on fully convolutional network in claim 4, wherein the method of the mentioned whitening treatment is to deduct a mean value of all training samples from the image digitized by the floating point of the standardization dimension and then divide it by the standard deviation of all training samples.

* * * * *